United States Patent [19]
Komiya et al.

[11] Patent Number: 5,468,635
[45] Date of Patent: Nov. 21, 1995

[54] IN VITRO METHOD FOR STIMULATING CELL GROWTH BY CULTURING CELLS IN A SERUM-FREE CULTURE MEDIUM COMPRISING HUMAN LYSOZYME

[75] Inventors: Koji Komiya; Tetsuya Takezono, both of Yokohama; Noritsugu Yabe; Hisao Matsui, both of Shimotsuga, all of Japan

[73] Assignee: Nippon Oil Co., Ltd., Japan

[21] Appl. No.: 243,074

[22] Filed: May 16, 1994

Related U.S. Application Data

[63] Continuation of Ser. No. 7,021, Jan. 21, 1993, abandoned, which is a continuation of Ser. No. 685,686, Apr. 16, 1991, abandoned.

[30] Foreign Application Priority Data

Apr. 17, 1990 [JP] Japan ..................... 2-100650
Feb. 15, 1991 [JP] Japan ..................... 3-042868

[51] Int. Cl.$^6$ ..................................... C12N 5/00
[52] U.S. Cl. .................. 435/240.21; 435/240.2; 435/240.3; 435/240.31
[58] Field of Search ............... 435/240.2, 240.3, 435/240.31, 240.21

[56] References Cited

U.S. PATENT DOCUMENTS 4,690,915  9/1987  Rosenberg ................... 514/2
4,839,290  7/1989  Kaieda et al. ............... 435/240.23

OTHER PUBLICATIONS

Sigma Chemical Co. 1981 Catalog p. 410.
Ruth E. Gordon, D. A. Barnett, J. E. Handorhan and C. H. Pang, *Nocardia coelica, N. autotrophica,* and the Nocardin Strain, Int. J. of Systematic Bacteriology 24:54–63, 1974.

ATCC catalogue of Cell Lines and Hybridomas, 16th edt. 1988, ATCC, Rockville, Md. pp. 3–5.

N. A. Dobrotina et al. [Lysozyme as a modulator], Vopr Med Khim 33(4):66–9, 1987.

J. R. Yanelli J. Imm. Meth. 139:1–6 1991.

Bjare et al., Pharmac. Ther., vol. 53, No. 3, pp. 355–374 (1992).

Jakoby et al., "Methods in Enzymology", vol. LVIII, published in 1979 by Academic Press, Inc. pp. 44–109.

Katsuta, H., "Kutritional Requirements of Cultured Cells", published in 1978 by University Park Press (Md.) pp. 1–21.

Barnes et al, Analytical Biochemistry, vol. 102, No. 2, pp. 255–269 (1980).

Oleinik et al, Immunologiya, O(3), pp. 78–81 (1982) (see biosis abstract) (translation attached).

*Primary Examiner*—Marian C. Knode
*Assistant Examiner*—Susan M. Dadio
*Attorney, Agent, or Firm*—Cushman Darby & Cushman

[57] ABSTRACT

The invention relates to an agent for promoting growth in animal cells. The agent contains a serum-free medium and lysozyme. The agent can optionally contain cytokines. The invention further relates to an in vitro method of stimulating the growth of T lymphoblastoid cells and peripheral blood lymphocytes, which comprises the step of culturing the T lymphoblastoid cells or peripheral blood lymphocytes in a serum-free culture medium comprising human lysozyme, as a growth stimulating agent, at a concentration of about 4–100 mg/liter.

5 Claims, 4 Drawing Sheets

IN VITRO METHOD FOR STIMULATING CELL GROWTH BY CULTURING CELLS IN A SERUM-FREE CULTURE MEDIUM COMPRISING HUMAN LYSOZYME

This is a continuation of application Ser. No. 08/007,021, filed on Jan. 21, 1993, now abandoned, which is a continuation of application Ser. No. 07/685,686, filed Apr. 16, 1991, now abandoned.

BACKGROUND OF THE INVENTION

1. Field of the Invention

The present invention relates to an animal cell growth-promoting agent and to a serum-free culture medium which contains the animal cell growth-promoting agent.

2. Description of the Prior Art

Conventionally, 5 to 20% of serum is usually added to a liquid culture medium for animal cells, in addition to amino acids, vitamins, sugars and inorganic salts. If the serum is removed, the cells stop growing and die off.

However, the use of the serum has several disadvantages; namely 1) the serum is so expensive as to amount to 75 to 95% of the total cost of the medium, 2) the serum is extremely different from one lot to another so that stable cell growth can not be attained, 3) the serum can not be sterilized by autoclaving so that contamination by mycoplasmas or viruses may occur, 4) the serum contains more than 500 kinds of proteins so that isolation and purification of physiologically active substances produced by cells are difficult. Consequently, serum-free culture media are used in order to solve these problems.

A number of serum-free culture media are known, i.e. a serum-free culture medium which contains Eagle's MEM (Minimum Essential Medium) as a basal culture medium and additional supplements such as albumin, insulin and transferrin and a serum-free culture medium which contains a modified Eagle's MEM as a basal culture medium supplemented with a cell growth factor obtained by fractionation of bovine serum using ammonium sulfate.

The above-mentioned serum-free culture media have been widely used for cultivation of animal cells. However, also they have problems; namely 1) their cell growth-promoting effect is less as compared to culture media containing serum, 2) serum components are substantially used although they are fractionated and 3) they are costly and not necessarily economical.

SUMMARY OF THE INVENTION

It is the principal purpose of the present invention to remove the above-mentioned disadvantages in the use of conventional serum-free culture media.

Namely, an object of the present invention is to provide an animal cell growth-promoting agent which contains no serum components.

Another object of the present invention is to provide a serum-free culture medium, which has the same or more activity in stimulating growth of animal cells as compared with the conventional serum-containing media, using none or the least possible amount of serum components.

A further object of the present invention is to provide a serum-free culture medium which makes it possible to isolate and purify animal cell products without difficulty.

Still a further object of the present invention is to provide a serum-free culture medium which can be used for multiplication of lymphocytes outsides the body (in vitro) in adoptive immunotherapy of cancer, in which the lymphocytes are taken from the body of a patient, particularly from that of a cancer patient and the lymphocytes are multiplied in vitro to reduce the capability in attacking the cancer cells and then returned to the body of the patient to kill the cancer cells.

In order to accomplish the above-mentioned objectives, the present inventors investigated various compounds for their activity in stimulating growth of animal cells and found that human lysozyme or lysozyme derived from other sources has extremely high capability in stimulating the growth of animal cells, thereby completing the present invention.

The present invention relates to an animal cell growth-promoting agent which contains lysozyme as an effective component. Furthermore, the present invention relates to a serum-free culture medium which contains lysozyme.

In accordance with the present invention, lysozyme in combination with cytokines can be used in a serum-free culture medium as an effective component. Among the cytokines, lymphokine is preferably used for this purpose.

BRIEF DESCRIPTION OF THE DRAWINGS

In FIG. 1, the results of culturing with the use of a medium without lysozyme, i.e. an NOC-909 medium, are plotted with closed circles and the results of culturing with the use of a medium supplemented with human lysozyme (40 mg/l), i.e. an NOC-909 medium, are plotted with double circles.

In FIG. 2, the results of culturing with the use of an RPMI 1640 medium supplemented with 10% of FBS are plotted with open circles, the results of culturing with the use of an NOC-909 medium without supplements are plotted with closed circles and the results of culturing with the use of an NOC-909 medium supplemented with human lysozyme (40 mg/l) are plotted with double circles.

In FIG. 3, the results with the use of a medium supplemented only with IL-2 are plotted with open circles, the results with the use of a medium supplemented with IL-2 and 100 mg/ml human lysozyme are plotted with closed circles and the results with the use of a medium supplemented with IL-2 and 20 mg/ml human lysozyme are plotted with double circles.

DETAILED DESCRIPTION OF THE INVENTION

Lysozyme is a protein which is found in mucous membranes of fish, animal tissues, plant tissues or the like and has enzymatic activity. Since lysozyme has a capability to dissolve various bacteria, it is known to be used as a food preservative, an antibacterial agent, a blood coagulating agent or pharmaceuticals such as anti-inflammatory agent.

Lysozyme is contained in a large amount particularly in hen's egg white and highly pure lysozyme can be isolated without great difficulty. Consequently, lysozyme derived from hen's egg is commonly used today in a preservative for food or the like and a medicinal ingredient added to an anti-inflammatory enzyme preparation or a cold remedy.

In the present invention, lysozyme derived not only from hen's egg but also from other sources, such as human lysozyme, bovine lysozyme, papaya lysozyme and T4 lysozyme is used. In particular, considering immuno-response by heterologous proteins, the use of human lysozyme has attracted a good deal of attention. Human lysozyme is preferably used also in the present invention. Human lysozyme is found in various human tissues and excretas such as the placenta, leukocytes, urea, breast milk and tears. Human lysozyme is now extracted in a purity of about 99% and is used for research.

Furthermore, the development of a method for industrial mass production of human lysozyme has been under investigation and Agency of Industrial Science Technology, Japan, has succeeded in expressing the synthetic human lysozyme gene by yeast and in extracellular excretion of the produced human lysozyme (Japanese Patent Laid-open No. 248488/1987). Furthermore, the present inventors in cooperation with Agency of Industrial Science Technology have improved the production conditions and have succeeded in overwhelmingly increasing the amounts of secretion and production of human lysozyme (Japanese Patent Laid-open No. 234673/1990).

The present invention was accomplished based on the finding that the above-mentioned human lysozyme is active in stimulating growth of animal cells such as lymphocytes, hybridomas and fibroblasts. Furthermore, this stimulating activity was found also in lysozyme derived from other tissues, e.g. egg white lysozyme, in the course of investigation by the present inventors.

However, since the stimulating activity is markedly high in human lysozyme, the use of human lysozyme is particularly preferable.

In the present invention, lysozyme may be used alone; however, lysozyme can be more effectively used in combination with a cytokine when lymphocytes are grown. The effect of lysozyme can be markedly increased particularly when lysozyme is used in combination with a lymphokine. Examples of the cytokine to be used include monokines and lymphokines. Examples of the monokine include a macrophage activating factor and a monocyte activating factor. Furthermore, examples of the lymphokines include interleukin 2, interleukin 3, interleukin 4, interleukin 6, a B-cell growth factor, a B-cell differentiation stimulating factor and gamma-interferon. Among them, interleukin 2 is particularly preferable. A cytokine may be added in advance to an animal cell culture medium or may be added simultaneously with lysozyme.

The animal cell growth-promoting agent according to the present invention may contain lysozyme alone or in combination with a cytokine. Furthermore, other growth-promoting factors such as albumin, insulin and transferrin may be combined with lysozyme and a cytokine. A part or all of the culture medium constituents may also be mixed with these growth-promoting factors to constitute the animal cell growth-promoting agent. The animal cell growth-promoting agent may be made into various forms such as powder, granule and liquid.

Furthermore, the serum-free culture medium according to the invention comprises a serum-free basal culture medium supplemented with an animal cell growth-promoting agent which contains lysozyme alone or lysozyme in combination with a cytokine and/or the above-mentioned constituents. As to the serum-free basal culture medium, any conventionally known serum-free basal culture medium can be used, unmodified or modified in any way as long as animal cells can grow in the medium. Examples of these media include ASF104 (Ajinomoto Co., Ltd.) and S-Clone SF-02 (Sanko Pure Chemical Industries, Ltd.). However, in particular, basal culture media which were developed by the present inventors, such as NOC-909, NOC-404 and NOC-905, are preferably used as the serum-free basal culture medium. Major constituents of the media NOC-909, NOC-905 and NOC-404 are shown in Table 1, Table 2 and Table 3, respectively.

Media used in the present invention may be either liquid media or solid media.

TABLE 1

| Major constituents of NOC-909 culture medium | |
|---|---|
| Constituents | Contents (mg/l) |
| Basal medium | |
| RPMI 1640 | |
| Eagle MEM | |
| Dulbecco's modified Eagle medium | |
| Powder medium containing the three basal culture media above | 9,830 |
| Amino acids | |
| L-Alanine | 20 |
| L-Glutamine | 300 |
| L-Arginine HCL | 15 |
| L-Asparagine ($H_2O$) | 15 |
| Glycine | 5 |
| L-Proline | 5 |
| L-Serine | 15 |
| L-Threonine | 15 |
| L-Valine | 15 |
| Vitamins | |
| Ascorbic acid-Na | 5 |
| Vitamin $B_{12}$ | 0.00125 |
| Biotin | 0.0025 |
| Other organic compounds | |
| Pyruvic acid-Na | 110 |
| d-Glucose | 100 |
| Choline chloride | 25 |
| Putrescine 2HCl | 0.0125 |
| Hypoxanthine | 0.025 |
| Thymidine | 0.0125 |
| Hormones | |
| Human apo-transferrin | 10 |
| Human insulin | 10 |
| Human serum albumin | 2,000 |
| Metals | |
| Ferrous sulfate ($7H_2O$) | 1 |
| Serenite-Na | 0.0017 |
| Buffers | |
| Glycylglycine | 1,500 |
| Sodium hydrogencarbonate | 1,400 |

TABLE 2

Major constituents of NOC-905 culture medium

| Constituents | Contents (mg/l) |
|---|---|
| Basal medium | |
| RPMI 1640 | |
| Eagle MEM | |
| Dulbecco's modified Eagle medium | |
| Powder medium containing the three basal culture media above | 9,830 |
| Amino acids | |
| L-Alanine | 20 |
| L-Glutamine | 300 |
| L-Arginine HCL | 15 |
| L-Asparagine (H$_2$O) | 15 |
| Glycine | 5 |
| L-Proline | 5 |
| L-Serine | 15 |
| L-Threonine | 15 |
| L-Valine | 15 |
| Vitamins | |
| Ascorbic acid-Na | 5 |
| Vitamin B$_{12}$ | 0.000125 |
| Biotin | 0.0025 |
| Other organic compounds | |
| Pyruvic acid-Na | 110 |
| d-Glucose | 100 |
| Choline chloride | 25 |
| Putrescine 2HCl | 0.0125 |
| Hypoxanthine | 0.0025 |
| Thymidine | 0.00125 |
| Hormones | |
| Human apo-transferrin | 10 |
| Human insulin | 10 |
| Metals | |
| Ferrous sulfate (7H$_2$O) | 1 |
| Serenite-Na | 0.0017 |
| Buffers | |
| Glycylglycine | 1,500 |
| Sodium hydrogencarbonate | 1,400 |

TABLE 3

Major constituents of NOC-404 culture medium

| Constituents | Contents (mg/l) |
|---|---|
| Basal media | |
| Eagle MEM | 4,560* |
| RPMI 1640 | 5,040* |
| Amino acids | |
| L-Arginine HCL | 15 |
| L-Asparagine (H$_2$O) | 15 |
| L-Glutamine | 300 |
| Glycine | 5 |
| L-Proline | 5 |
| L-Serine | 30 |
| L-Threonine | 15 |
| L-Valine | 15 |
| Vitamins | |
| Cyanocobalamin | 0.01 |
| Biotin | 0.01 |
| Pantothenic acid-½ Ca | 10 |
| Choline chloride | 25 |
| Other organic compounds | |
| d-Glucose | 500 |
| d-Mannose | 100 |
| Pyruvic acid-Na | 110 |
| Putrescine-2 HCl | 0.02 |
| Hypoxanthine | 0.1 |
| Thymidine | 0.025 |
| Ethanolamine | 20 |
| Hormones | |
| Human insulin | 10 |
| 3,3',5-Triiodo-L-thyronine-Na | 0.0065 |
| Metals | |
| Ferric chloride (6H$_2$O) | 5 |
| Copper sulfate (5H$_2$O) | 0.00002 |
| Selenous acid | 0.00002 |
| Zinc acetate (2H$_2$O) | 0.0014 |
| Chelating agents and buffers | |
| Dihydroxyethylglycine | 815 |
| Glycylglycine | 1,125 |
| Sodium hydrogencarbonate | 1,400 |

*½ of the ordinary concentration

A concentration of lysozyme in the serum-free culture medium may be 0.1–2,000 mg, preferably about 0.5–500 mg and more preferably 10–200 mg, per one liter of serum-free culture medium. When human lysozyme is used, the concentration particularly preferable is about 10–200 mg per one liter of medium. Furthermore, a concentration of a cytokine may be 1–2,000 unit/ml, preferably 10–1,000 unit/ml per one milliliter of the serum-free culture medium. Furthermore, when a lymphokine is used, a concentration also in this range can be used. Among the lymphokines, interleukin-2 (IL-2) is particularly preferable and used at a concentration of 10–1,000 Units per one milliliter of the medium.

Furthermore, bovine serum albumin (BSA) or the like can be additionally used in the serum-free culture medium as far as the object of the present invention is not disturbed. In other words, the serum-free culture medium according to the present invention also includes a culture medium in which a BSA concentration is less than that in a conventional culture medium with serum.

The present invention can be applied to the culture of animal cells such as lymphocytes, e.g. human cells derived from peripheral blood acute lymphoblastic leukemia, hybridomas, e.g. anti-HBs antibody-producing hybridomas and fibroblasts.

In particular, the invention can be applied to the culture of lymphocytes, i.e. T-cells (helper cells, suppressor cells, killer cells or the like) and B-cells or NK-cells (Natural Killer cells).

With the use of the serum-free culture medium in accordance with the present invention, the growth of animal cells is stimulated so that physiologically active substances produced by the animal cells can be effectively recovered without being affected by the serum components.

Furthermore, a characteristic advantage of the present invention will be explained as follows:

Recently, the vital cell transplant therapies have been developed mainly in the United States. Also in Japan, the research on these therapies has been activated.

Examples of the living cells graft therapies include an adoptive immunotherapy for cancer, an autogenous marrow cell graft therapy, an autogenous skin fibroblasts graft therapy, graft of fetal Langerhans' islands primary cells to a diabetes mellitus patient, transplant of fetal neurocytes to a Parkinson's disease patient and graft of fetal liver cells to a hemophilia patient.

In the adoptive immunotherapy, lymphocytes are taken out from the body of a cancer patient and are proliferated in vitro; after stimulating their attacking ability, the cells are returned to the body of the patient to kill the cancer cells. Furthermore, in some cases, cancer cells are taken out and lymphocytes are taken from the blood and then they are cultured together to selectively propagate killer T-cells; the resulting killer T-cells are administered to a cancer patient. These therapeutic methods have less serious side effects as compared to those with the use of cancer controlling agents because lymphatic cells are selected; furthermore, they are effective to metastatic cancers because the lymphatic cells circulate in the body. There are three kinds of adoptive immunotherapy as follows:

(1) LAK (Lymphokine Activated Killer) Cells Therapy

In this method, lymphocytes are taken from the peripheral blood and are cultured in vitro with IL-2 for activation; the resulting cells (LAK cells) are then returned to the body. The method is advantageous because it requires a relatively short period of time for culturing (3–7 days). The disadvantages are that LAK cells are less specific to cancer cells and are poorly accumulated onto cancerated tissues and that LAK cells have to be administered with a large amount of IL-2.

(2) TIL (Tumor Infiltrating Lymphocytes) Therapy

Lymphocytes are taken from a site of carcinoma since killer cells which specifically attack cancer cells are present in high density at the site of cancer. The obtained lymphocytes are cultured in vitro with IL-2 and returned to the body. TILs are 50–100 times more active than LAK cells and are characterized in their high specificity and accumulable property, but a long period of time (30–60 days) is required for the cultivation.

(3) CIL (Cytotoxic T Lymphocytes) Therapy

Lymphocytes are taken from the peripheral blood and separately cancer cells are isolated from a site of carcinoma; the lymphocytes and cancer cells are mixed and are cultured in vitro with IL-2 to induce killer T-cells and then the resulting killer T-cells are returned to the body. The killer cells are highly specific to carcinoma cells and are highly accumulable onto cancerated tissues; this method has disadvantages such that it is difficult to isolate cancer cells and that an inactivating agent (anti-cancer agent) has to be administered in advance to a cancer patient to be treated in order to inactivate suppresser T-cells.

Accordingly, in order to further develop the above-mentioned therapies, it is necessary to grow lymphocytes effectively. In these therapies, the primary importance is how to effectively and safely grow cells such as lymphocytes, marrow cells and skin fibroblasts in vitro on a culture medium.

Furthermore, when the serum is used as a constituent of the culture medium, these therapies have further disadvantages such that mycoplasma or virus infection may occur as mentioned above, that cells having a certain quality are difficult to obtain so that it is very difficult to standardize the cell growth and that the production cost is high. In order to overcome these disadvantages, the use of serum-free media is desired and, at the same time, development of growth factors to be used in the serum-free media has become of primary importance. In the present invention, based on the finding that lysozyme is effective as a growth factor, lysozyme was used so that growth of animal cells are extremely stimulated as compared to those with the use of serum and the above-mentioned problems are solved; thereby the present invention greatly promotes the further development of the living cells graft therapy.

On the other hand, as to monoclonal antibodies, considerable attention has been called to their applications in diagnosis of infections or the like, in purification of physiologically active substances using affinity chromatography or the like, in medical treatment in a target therapy or in other researches. Lysozyme in accordance with the present invention stimulates the growth and antibody producing activity of hybridomas so that it becomes possible to produce various monoclonal antibodies to be used for the above-mentioned applications at low cost. Furthermore, with the use of lysozyme, there is no need to worry about variations in quality from one lot to another, as observed with the use of serum, due to the difference in sampling and storage methods. Consequently, a process for antibody purification is extremely simplified, which facilitates monoclonal antibody production.

The present invention will be more clearly understood with reference to the following examples.

EXAMPLE 1

A series of serum-free culture media were obtained by supplying 4–100 mg/l of human lysozyme to NOC-909 culture media having the composition shown in Table 1.

Into the resulting media were inoculated CEM cells, as an example of the cells of T-lymphoblast-like etablished cell line derived from human peripheral blood acute lymphoblastic leukemia, which had been adapted to the NOC-909 medium, at a concentration of $1\times10^4$ cells/ml. Cultivation of the cells was carried out at 37° C. with blowing $CO_2$ at a concentration of 5%. Cell counts at day 3 of the cultivation was shown in Table 4.

As shown in Table 4, lysozyme has a satisfactory cell growth-promoting effect when added at concentrations 4–100 mg/l, preferably 10–40 mg/l, that is, the number of cells/ml greatly increased by 40% as compared with those without lysozyme.

TABLE 4

| Effect of addition of human lysozyme | |
| --- | --- |
| Amount of lysozyme added (mg/l) | Number of cells/ml at day 3 |
| 0 | $10.2 \times 10^4$ |
| 4 | $14.4 \times 10^4$ |
| 10 | $14.7 \times 10^4$ |
| 40 | $14.8 \times 10^4$ |
| 100 | $14.3 \times 10^4$ |

EXAMPLE 2

A serum-free culture medium was obtained in the same manner as described in Example 1, except that human lysozyme was added at a concentration of 40 mg/l to the medium. Into the resulting medium were added CEM cells (ATCC CCL119), which had been adapted to a NOC-909 medium, at a concentration of $1\times10^4$ cells/ml. Cultivation of the cells was carried out at 37° C. for 6 days with blowing $CO_2$ at a concentration of 5%.

As to controls, the cultivation was carried out in the same manner as described above, except that no human lysozyme was added to the medium.

Figure 1:
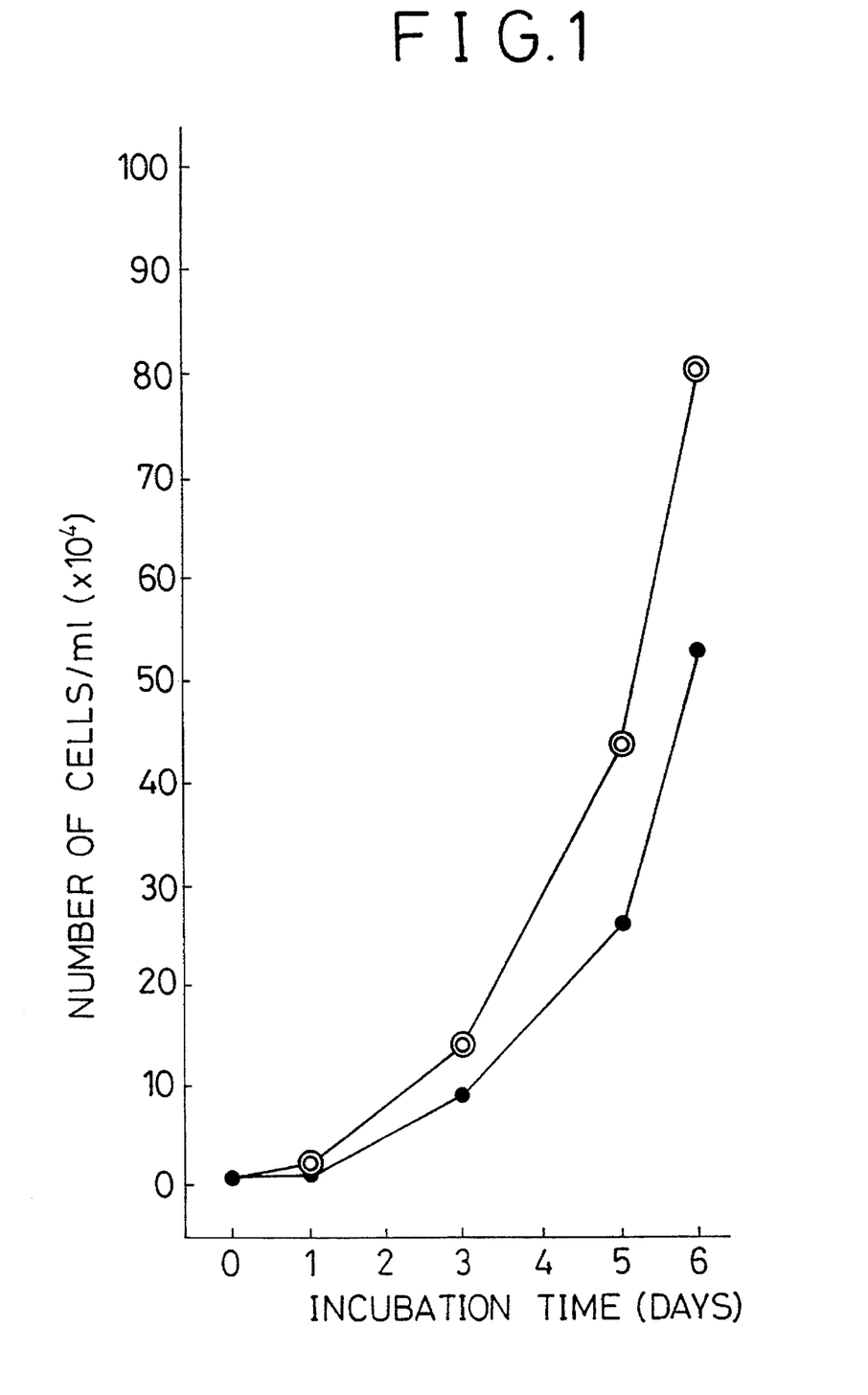
FIG. 1 shows the results of culturing animal cells, i.e. CEM-cells (ATCC CCL119) which were adapted to an NOC-909 medium, in Example 2 according to the present invention.

The results are shown in FIG. 1, in which the growth of CEM cells during cultivation is demonstrated. As shown in the FIG. 1, the number of cells increased with the increase in the number of days of cultivation. Furthermore, it is clearly shown that the number of cells in the medium supplemented with human lysozyme is higher than those in the medium without human lysozyme, which indicates that the lysozyme stimulates the cell growth.

A serum-free culture medium was prepared in the same manner as described in Example 1, except that human lysozyme was added at a concentration of 40 mg/l to the medium. Into the resulting medium were added ALL cells, which were in a process of adaptation to a NOC-909 medium, at a concentration of $1\times10^5$ cells/mi. Cultivation of the cells was carried out at 37° C. for 4 days with blowing $CO_2$ at a concentration of 5%.

As to controls, the cultivation was carried out in the same manner as described above, except that no human lysozyme was added to the medium.

The numbers of the ALL cells at day 2 and day 4 are shown in Table 5. As clearly shown in Table 5, the cell growth was more significantly stimulated in the culture medium supplemented with human lysozyme than in the culture without human lysozyme, which indicates that human lysozyme is effective independent of which kinds of cell are used.

TABLE 5

| | Growth of ALL cells | |
|---|---|---|
| | Cells/ml at day 2 | Cells/ml at day 4 |
| NOC-909 culture medium | $35.9 \times 10^4$ | $53.5 \times 10^4$ |
| +40 mg/l human lysozyme | $50.3 \times 10^4$ | $77.7 \times 10^4$ |

EXAMPLE 3

A serum-free culture medium was prepared by adding human lysozyme at a concentration of 40 mg/l to an NOC-909 medium. Into the resulting medium were inoculated CEM cells, which had been adapted to a NOC-909 medium, at a concentration of $1\times10^4$ cells/mi. Cultivation of the cells was carried out at 37° C. for 7 days with blowing $CO_2$ at a concentration of 5%.

As to controls, the above-mentioned CEM cells were cultivated in the same manner as described above in an NOC- 909 medium without human lysozyme or a serum culture medium in which 10% of normal serum (FBS) was added to a serum-free basal culture medium RPMI 1640 (a commercially available product of Gibco Laboratory) which is ordinarily used for lymphocytes. Cultivation was carried out in the same manner as described above. The results are shown in FIG. 2.

Figure 2:
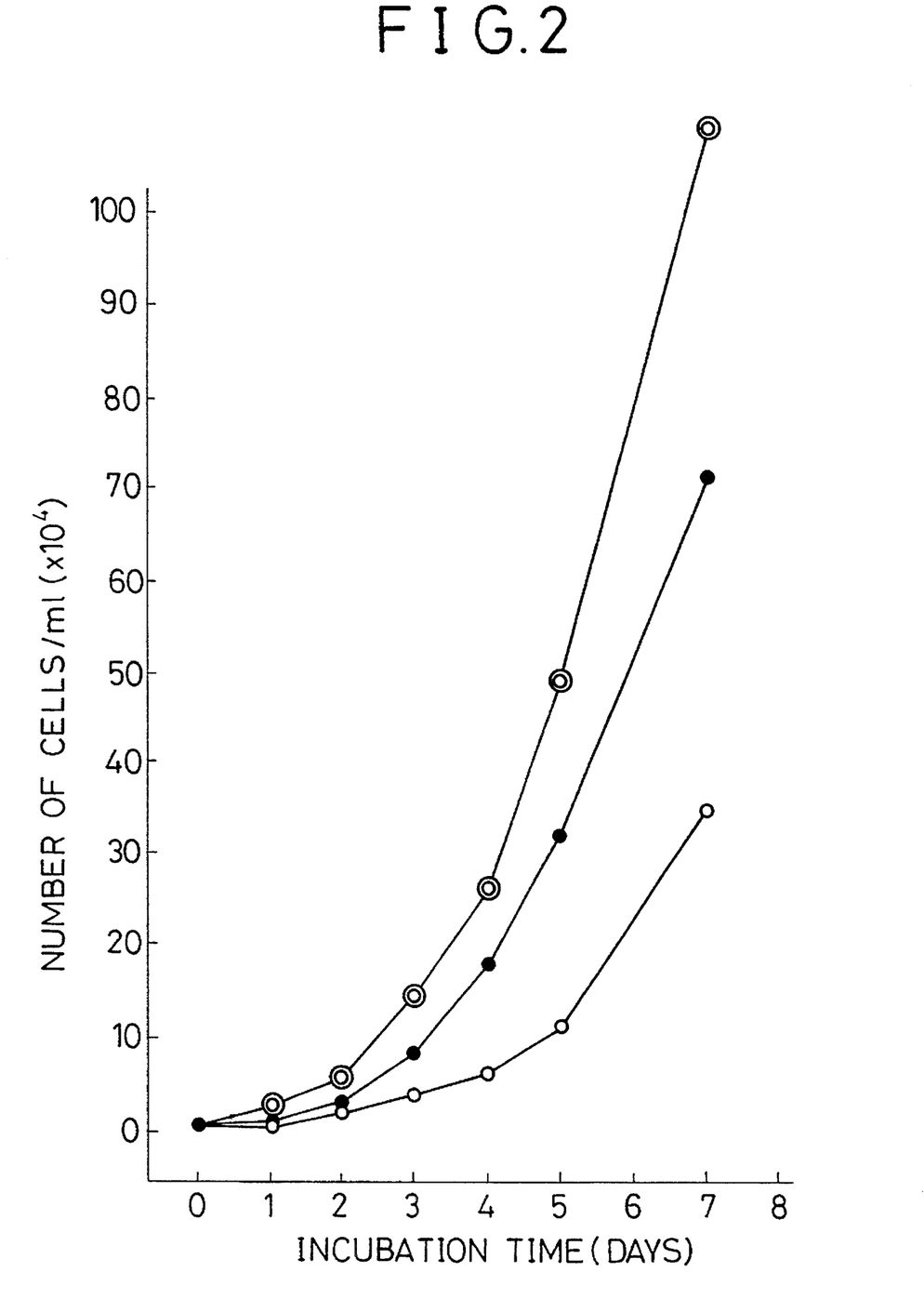
FIG. 2 shows the results of cultivating the CEM cells which were adapted to an NOC-909 medium.

As shown in FIG. 2, the growth of the NOC-medium-adopted CEM cells was more significantly stimulated in the NOC-909 medium supplemented with human lysozyme than in the culture medium supplemented with FBS.

EXAMPLE 4

Human peripheral blood was drawn and silica gel, latex or carbonyl iron, as a phagocytic agent, was added to the blood at a concentration of about 10%. The resulting mixture was incubated at 37° C. for one hour to isolate lymphocytes using an ordinary method. The lymphocytes were suspended in a serum-free culture medium (NOC-905) to count the cell number.

Subsequently, the lymphocytes were inoculated into a NOC-905 medium supplemented with human lysozyme (HLY) and IL-2 to get a starting lymphocyte concentration of $5\times10^5$/ml and cultured using a 96-well plate (6–10 series) having a capacity of 0.2 ml/well; thus, the relation between the concentrations of HLY and IL-2 added and the growth of the lymphocytes was investigated. At day 4 after the incubation, $^3$H-thymidine was added to the culture medium and the cultivation was further continued for 4 hours to incorporate the thymidine into the lymphocytes.

Subsequently, the lymphocytes were adsorbed onto a filter and then washed with pure water. The filter was immersed in a scintillation cocktail and capacity of the lymphocyte to incorporate $^3$H-thymidine (DNA synthesizing capacity) was determined by measuring the amount of beta-ray generated by $^3$H-thymidine.

Figure 3:
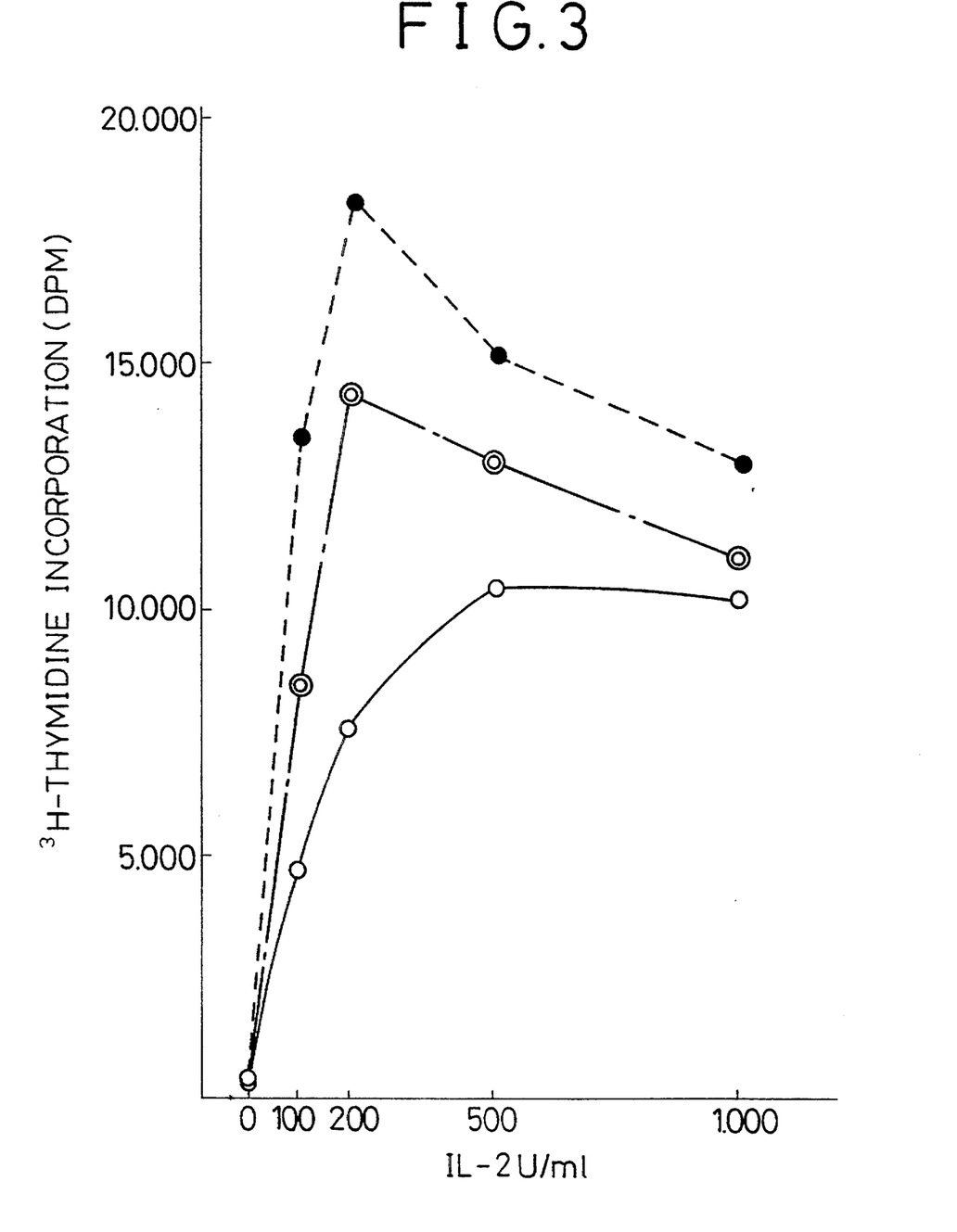
FIG. 3 shows changes in the amount of thymidine incorporated according to the changes in the concentration of interleukin-2 (IL-2) in the medium in Example 4 of the present invention.

The results are shown in FIG. 3. As demonstrated in FIG. 3, a generally known phenomenon that the amount of incorporated thymidine increases depending on the IL-2 concentration was confirmed. The amount of incorporated thymidine was larger when IL-2 was used alone than when IL-2 was used in combination with human lysozyme; further, an IL- 2 concentration to maximize the thymidine incorporation was 500 units/ml when IL-2 was used alone but it was decreased to 200 units/ml when IL-2 was used in combination with human lysozyme; thus the amount of IL-2 used in an adoptive immunotherapy can be decreased. Further, IL-2, when used in combination with human lysozyme, is preferably used at a concentration of about 200 units/ml.

EXAMPLE 5

Figure 4:
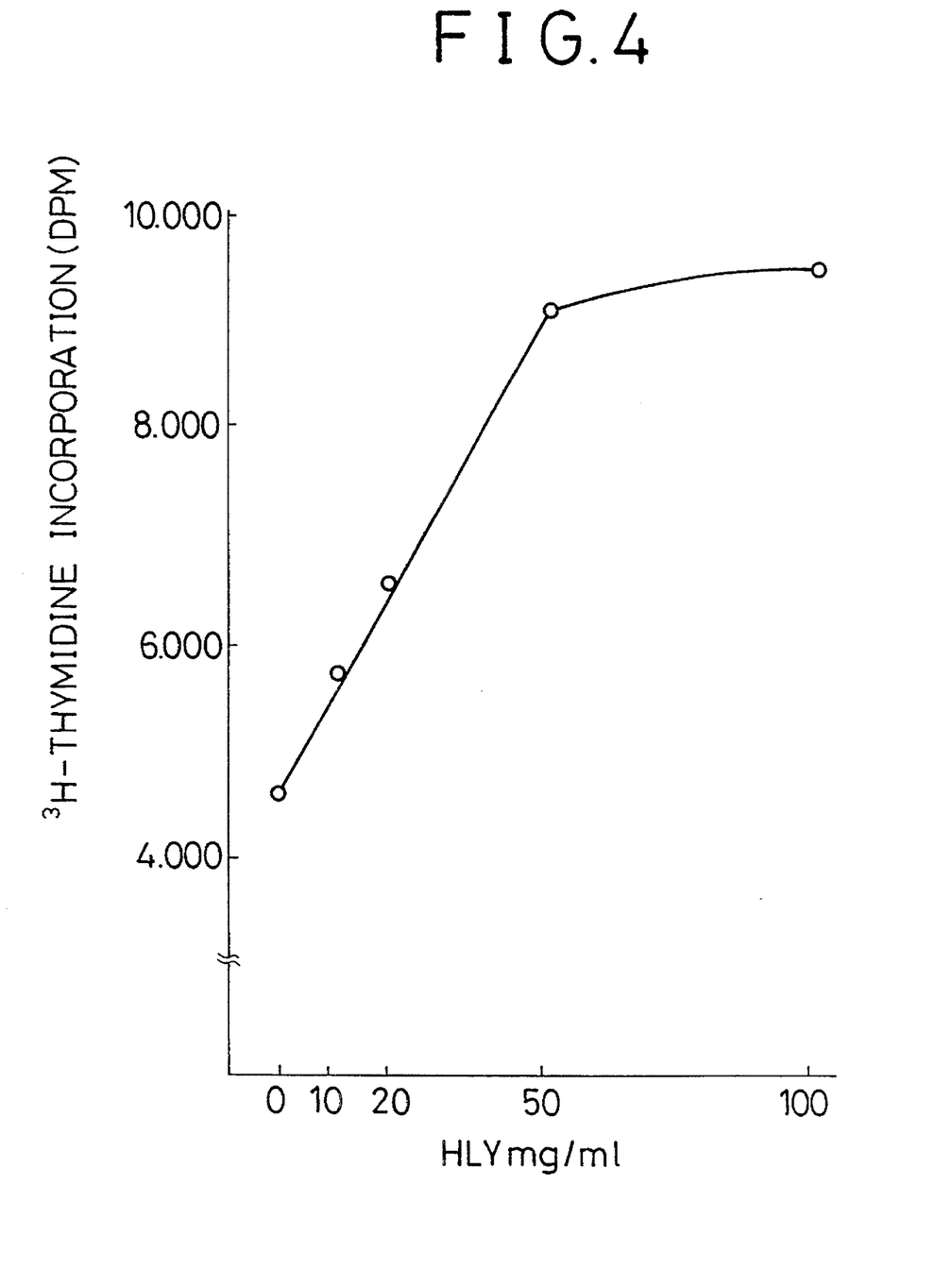
FIG. 4 shows changes in the amount of thymidine incorporated according to the changes in concentration of human lysozyme in the medium in Example 5 of the present invention.

Human lymphocytes were cultured and the amount of incorporated thymidine was measured in the same manner as described in Example 4, except that an NOC-905 medium supplemented with 200 units/ml of IL-2 and 0–100 mg/l of human lysozyme was used for the cultivation. The results are shown in FIG. 4. As indicated in FIG. 4, the amount of incorporated thymidine increases depending on the concentration of human lysozyme in the same way as shown in FIG. 3; however, the increase rate of the incorporation decreased after the human lysozyme concentration reached about 50 mg/l.

EXAMPLE 6

Human lymphocytes were cultured and the amount of incorporated thymidine was determined in the same manner as described in Example 5, except that NOC-905 media supplemented with 200 units/ml of IL-2 was further supplemented with 100 mg/l of human lysozyme (HLY) or 100 mg/l of chicken egg white lysozyme (CLY). The results are shown in Table 6.

TABLE 6

| Medium | Amount incorporated (DPM) |
|---|---|
| NOC-905 | 146.8 ± 20.5 |
| NOC-905 + IL-2 200 U/ml | 4195.4 ± 430.1 |
| NOC-905 + IL-2 200 U/ml + HLY 100 mg/l | 9617.0 ± 799.4 |
| NOC-905 + IL-2 200 U/ml + CLY 100 mg/l | 6241.2 ± 843.1 |

EXAMPLE 7

Lymphocytes were isolated and purified in the same, manner as described in Example 4 and were inoculated into an NOC-909 medium or NOC-905 medium supplemented with IL-2 and human lysozyme (HLY), wherein a starting lymphocyte concentration was $5\times10^5$/ml and a 24-well plate having a capacity of 0.5 ml/well was used for culture. The lymphocytes were subcultured about twice a week (a half of the medium was freshly exchanged at first and ⅕ thereafter). As the subculturing proceeded, the number of cells increased so that the 24-well plate culture vessel was replaced with a 3.5 cm-diameter petri dish, to a 6 cm-diameter petri dish and then to a 25 ml- volume flask, successively.

At appropriate intervals during the subculturing period, microscopic observations were carried out to investigate the presence and absence of viable lymphocytes. The results are shown in Table 7.

As shown in Table 7, when the serum-free culture media, especially the NOC-905, supplemented with human lysozyme was used, the survival time of the lymphocytes was markedly extended due to the addition of human lysozyme and moreover the subculture was able to continue for a longer period of time.

TABLE 8

| Basal culture medium | IL-2 (U/ml) | HLY (mg/l) | Surviving period (Weeks) | Subculturing (Times) |
|---|---|---|---|---|
| NOC-909 | 500 | 0 | 3 | 4 |
| NOC-909 | 500 | 100 | 5 | 8 |
| NOC-905 | 500 | 0 | 8 | 14 |
| NOC-905 | 500 | 20 | 15 | 28 |
| NOC-905 | 500 | 100 | 18 or more | 34 or more |

What is claimed is:

1. An in vitro method for stimulating the growth of T lymphoblastoid cells and peripheral blood lymphocytes comprising culturing said T lymphoblastoid cells or peripheral blood lymphocytes in a serum-free culture medium comprising human lysozyme, as a growth-stimulating agent, in a concentration of about 4–100 mg/liter.

2. The method of claim 1, wherein said serum-free culture medium further comprises a cytokine.

3. The method of claim 2, wherein said cytokine is a lymphokine.

4. The method of claim 3, wherein said lymphokine is an interleukin.

5. The method of claim 1, wherein said peripheral blood lymphocytes are human peripheral blood lymphocytes requiring interleukin-2 for growth and said serum-free culture medium further comprises interleukin-2.

* * * * *